(12) United States Patent
Hofvander et al.

(10) Patent No.: US 8,699,011 B2
(45) Date of Patent: Apr. 15, 2014

(54) TIME-SYNCHRONIZED TDLAS MEASUREMENTS OF PRESSURE AND TEMPERATURE IN A GAS TURBINE ENGINE

(75) Inventors: Henrik Hofvander, Boulder, CO (US); Bernard P Masterson, Louisville, CO (US); Andrew D Sappey, Lakewood, CO (US); James Howell, Louisville, CO (US); David Owenby, Erie, CO (US); Lee Sutherland, Longmont, CO (US); Michael J Estes, Longmont, CO (US)

(73) Assignee: Zolo Technologies, Inc., Boulder, CO (US)

( * ) Notice: Subject to any disclaimer, the term of this patent is extended or adjusted under 35 U.S.C. 154(b) by 1 day.

(21) Appl. No.: 13/696,630

(22) PCT Filed: May 10, 2011

(86) PCT No.: PCT/US2011/035954
§ 371 (c)(1),
(2), (4) Date: Nov. 7, 2012

(87) PCT Pub. No.: WO2011/143240
PCT Pub. Date: Nov. 17, 2011

(65) Prior Publication Data
US 2013/0057864 A1    Mar. 7, 2013

Related U.S. Application Data

(60) Provisional application No. 61/333,143, filed on May 10, 2010.

(51) Int. Cl.
*G01N 21/90* (2006.01)
*G01N 21/00* (2006.01)

(52) U.S. Cl.
USPC ............................. 356/73; 356/435; 356/437

(58) Field of Classification Search
CPC ...... G01J 2001/4242; G01J 3/4338; G01J 5/0014
USPC .......... 356/300–334, 434–435, 484, 478, 482
See application file for complete search history.

(56) References Cited

U.S. PATENT DOCUMENTS 4,053,227 A    10/1977    Bodlaj
6,080,983 A *   6/2000    Waczynski et al. ...... 250/231.16
(Continued)

OTHER PUBLICATIONS

Yichao Chen. "Multiplexed fiber Fabry—Perot temperature sensor system using white-light interferometry", Jun. 1, 2002 Optics Letters.*

(Continued)

*Primary Examiner* — Kara E Geisel
*Assistant Examiner* — Maurice Smith
(74) *Attorney, Agent, or Firm* — Swanson & Bratschun, L.L.C.

(57) ABSTRACT

A method of absorption spectroscopy to determine a rapidly variable gas parameter. The method includes transmitting light from a synchronization light source to a synchronization detector. The transmitted light is periodically interrupted by a moving mechanical part between the synchronization light source and synchronization detector. The output from the synchronization detector is used to generate a repeating time signal having variable phase delay. This signal is used to control the timing of laser spectroscopy wavelength scans. Multiple spectroscopic scans may be repeated at multiple selected time signal phase delay and the results averaged for each phase. Apparatus for implementing the above methods are also disclosed.

15 Claims, 4 Drawing Sheets

(56) References Cited

U.S. PATENT DOCUMENTS

| | | |
|---|---|---|
| 7,248,755 B2 | 7/2007 | Sappey et al. |
| 2006/0061770 A1* | 3/2006 | Erskine .................. 356/484 |
| 2006/0133714 A1 | 6/2006 | Sappey et al. |
| 2008/0002186 A1 | 1/2008 | Masterson et al. |
| 2008/0285916 A1 | 11/2008 | Sappey et al. |
| 2008/0289342 A1 | 11/2008 | Sappey et al. |
| 2010/0080500 A1* | 4/2010 | Zheng et al. .................. 385/12 |

OTHER PUBLICATIONS

International Search Report and Written Opinion for Application No. PCT/US2011/035954 (Sep. 6, 2011).

* cited by examiner

TIME-SYNCHRONIZED TDLAS MEASUREMENTS OF PRESSURE AND TEMPERATURE IN A GAS TURBINE ENGINE

BACKGROUND

The optimization of the design or configuration of several critical mechanical components in a gas turbine engine cannot presently be realized with conventional analysis techniques. Conventional optimization and design techniques fail because computational fluid dynamic models for systems such as a gas turbine engine are not sufficiently validated to insure accuracy. For example, it would be highly desirable to optimize the design of gas turbine compressor blades. Valid results must be based upon accurate fluid dynamic modeling of the pressure, temperature and flow rates of gasses within the compressor environment. The development of suitably accurate models would require the measurement of pressure with two-dimensional spatial resolution and high temporal resolution. Such measurements are not currently possible.

In general, the measurements of gas pressure and flow over time may be made with selected spectroscopic techniques, for example tunable diode laser absorption spectroscopy (TDLAS). For example, the TDLAS measurement of selected combustion parameters is described in U.S. Pat. No. 7,248,755 titled; Method and Apparatus for the Monitoring and Control of Combustion, which patent disclosure is incorporated herein by reference for all matters disclosed therein. The primary difficulty in making TDLAS measurements in a gas turbine compressor or other highly variable environment involving rapidly moving mechanical components is a lack of sufficient signal to noise available in the short time duration available to average the acquired spectra while still maintaining adequate temporal resolution. For example, distributed feedback (DFB) diode lasers can be tuned over a spectral range of a few tenths of a nanometer at up to a few 10's of kilohertz which allows measurements to be made at perhaps a 1 kHz update rate given the averaging required to produce good SNR in the turbulent environment of a gas turbine engine. Such an update rate can be adequate for path averaged measurements in the hot section of the engine. However, in order to map the temperature or pressure field in the compressor zone and to provide adequate temporal resolution to "freeze" the motion of the compressor blades relative to the stators requires a different measurement method with enhanced temporal resolution characteristics.

A brief calculation will serve to illustrate the challenges presented by any attempt to use standard wavelength-scanned methods of making TDLAS measurements to measure pressure in the compressor environment with high temporal resolution. Compressor blade assemblies typically rotate at approximately 10,000 rpm.

10000 rpm=167 revolutions/second

A compressor assembly might consist of approximately 60 compressor blades for a low pressure compressor, which means that compressor blades pass by a particular stator at a frequency of 10 kHz. Given that it is only possible to scan a laser across the necessary absorption frequencies a few times faster than this rate; and in view of the requirement to average many scans to produce a spectrum with sufficient SNR for analysis, conventional TDLAS strategies lack the necessary temporal resolution to "freeze" the motion of the compressor blades and see the temporal pressure transients that must be observed and studied. The embodiments disclosed herein are directed toward overcoming one or more of the problems discussed above.

SUMMARY OF THE EMBODIMENTS

One embodiment disclosed herein is a method of TDLAS measurement which includes providing a synchronization light source and synchronization detector. Light may be transmitted from the synchronization light source to the synchronization detector. In addition, the light transmitted from the synchronization source to the synchronization detector may be periodically interrupted, extinguished, reflected, refracted or otherwise disturbed in between the synchronization light source and synchronization detector.

The output from the synchronization detector may be used to generate a repeating time signal having variable phase delay. The time signal is thus coordinated with a moving mechanical part, for example compressor rotor blades, that periodically interrupt the light transmitted from the synchronization light source to the synchronization detector. This signal may be used to control a first DFB laser spectroscopy wavelength scan by commencing the scan at a selected time signal phase delay. Multiple spectroscopic scan may be repeated at subsequent instances of the selected time signal phase delay and the results averaged. In addition, the method may include initiating subsequent scans at an alternative time signal phase delay. The subsequent scans at alternative time signal phase delays may be repeated as necessary and averaged to achieve a sufficient signal for spectroscopic analysis. In this manner a parameter such as gas pressure, gas temperature or gas flow rate may be determined as a function of time using known absorption spectroscopy techniques even though the parameter is varying over a very short period of time.

An alternative embodiment is a laser spectroscopy apparatus comprising a spectroscopic probe laser source and detector and a synchronization light source and synchronization detector. The apparatus may further include an electronic delay generator which receives input from the synchronization detector and provides a time signal to control the spectroscopic probe laser source as described above.

An alternative embodiment is a method of measuring a transient pressure in a gas turbine engine. The method includes controlling an absorption spectroscopy probe with a time signal generated according to the output of a synchronization detector as described above.

DETAILED DESCRIPTION

Figure 1:
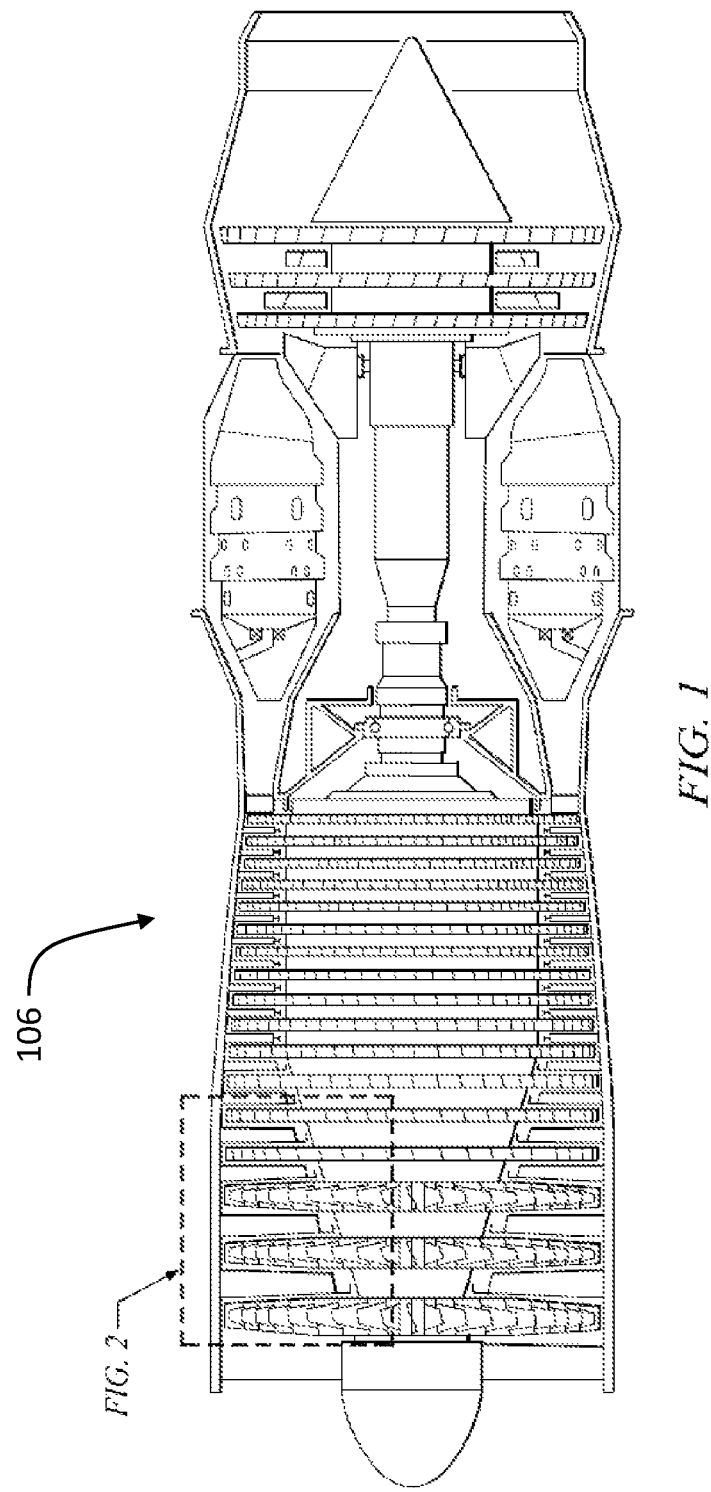
FIG. 1 is a schematic diagram of a gas turbine engine.

In the following detailed description of the embodiments, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the present inventions. The following detailed description is therefore, not to be taken in a limiting sense, and the scope of the present inventions is defined only by the appended claims.

Unless otherwise indicated, all numbers expressing quantities of ingredients, dimensions reaction conditions and so forth used in the specification and claims are to be understood as being modified in all instances by the term "about". In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

The embodiments of the current disclosure include methods that allow adequate temporal resolution to be obtained with the absorption spectroscopy measurement or wavelength multiplexed TDLAS measurement of fluid parameters such as pressure, temperature or gas flow rate in a complex system having rapidly moving mechanical parts; such as the compressor section of a gas turbine engine. The disclosed methods feature the synchronization of spectroscopic measurements with the periodic motion of a mechanical part of the apparatus. The part may be the part which is generating the local pressure, temperature or flow gradient(s) being measured. This disclosure includes a comprehensive discussion of measurements made in the compressor section of aircraft turbine engines where gas pressure measurements are synchronized to the motion of the turbine rotor. The techniques described herein could however be equally well applied to reciprocating engines such as the piston engine of an automobile or other rapidly moving structures that produce rapidly evolving, cyclical, local pressure, temperature or flow gradients of interest. One specific application of the disclosed methods is for the measurement of pressure with relatively high spatial and temporal resolution, but the described technique and apparatus could equally well be used to measure temperature or flow with high spatial and temporal resolution.

The methods and apparatus disclosed herein may be implemented to control any type of absorption spectroscopy, including but not limited to tunable diode laser absorption spectroscopy (TDLAS). The methods and apparatus disclosed herein may specifically be implemented to control the spectroscopic analysis of a system with a very high degree of time precision. Various absorption spectroscopy methods have been developed which are more or less suitable for sensing gas flow, gas temperature or gas pressure. Commonly known techniques are wavelength modulation spectroscopy and direct absorption spectroscopy. Each of these techniques is based upon a predetermined relationship between the quantity and nature of laser light received by a detector after the light has been transmitted through a measurement zone and absorbed in specific spectral bands which are characteristic of the gas species present in the measurement zone. The absorption spectrum received by the detector is processed according to known techniques to determine parameters of interest, for example pressure and temperature when the gas composition is known. The non-contact nature of laser absorption spectroscopy makes it well-suited for harsh environments where other probes cannot be used.

Effective sensing of temperature or pressure may require the performance of TDLAS with multiple widely spaced frequencies of laser light. The frequencies selected must match the absorption lines of the transitions being monitored. The strength of a molecular absorption is a function of temperature and pressure. Thus, a particular advantage of TDLAS with a wavelength-multiplexed probe beam is increased accuracy of temperature or pressure measurements. In the sensing systems of the present invention, temperature and pressure may be determined by measuring the ratio of the intensity of two or more molecular lines, for example water lines. The methods and apparatus disclosed herein provide for the precise temporal control of TDLAS to determine a parameter, pressure for example, within a system such as a jet turbine engine where local pressures vary at a very rapid rate.

It is illustrated above that the temporal resolution available with conventional TDLAS techniques where a DFB laser is scanned at a few tens of kHz is inadequate for the analysis of the pressure environment within a gas turbine engine. The novel phase locking methods disclosed herein may be implemented to create sufficient temporal resolution without unduly increasing the DFB scan rate. The methods include the generation of a light-based synchronization pulse. A synchronization pulse can be generated in any number of ways but one possibility involves detecting the extinction of a laser, LED or other light source by a moving mechanical surface. For example a laser output, LED output or the output from another light source directed to a detector may be repetitively blocked and wholly or partially extinguished by compressor blades or another moving part which passes through the synchronization beam path. One representative, but non-exclusive implementation of a synchronization pulse source and detector is the synchronization system 100 illustrated on FIG. 2 which is a detailed view of the compressor rotor 102 and stator 104 elements of the jet turbine engine 106 of FIG. 1.

The synchronization system 100 includes a synchronization light source 108 and a corresponding detector 110 in intermittent optical communication with the light source 108. The synchronization light source 108 can be implemented with a laser, LED or other type of light source and the synchronization detector 110 can be any type of suitable corresponding photo-detector element. The synchronization light source 108 and synchronization detector 110 can be positioned in any location where a synchronization beam 112 projected from the light source to the detector is positioned to be periodically wholly or partially extinguished by one or more moving mechanical parts, for example compressor rotors 102. Thus, the position of the light source 108 before the compressor section of an engine and the position of the detector 110 on a stator 104 is merely one example and not intended to be limiting.

Alternatively the system could be implemented with a light source and detector positioned such that the synchronization beam is periodically reflected to the detector as opposed to being periodically extinguished. In a reflection embodiment, the light source and detector could share a single housing. Alternatively the synchronization beam could be reflected, wholly or partially extinguished, routed in a waveguide, refracted or otherwise interrupted provided that the synchronization beam is periodically affected by at least one moving mechanical part. The moving part is illustrated in FIG. 2 as a series of functional rotors; the moving part could be implemented as a dedicated part linked to the engine 106 which serves no purpose other than light interruption.

Figure 3:
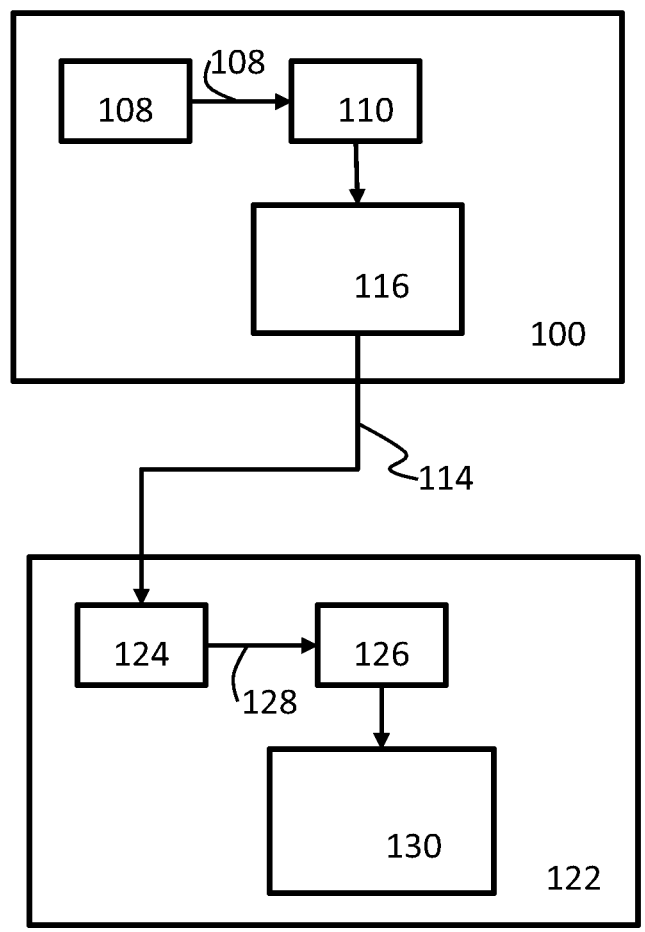
FIG. 3 is a chart of a transient pressure gradient generated when compressor rotors pass a stator over time.

The detector 110 will convert light from the synchronization beam 112 into an electrical or optical synchronization time signal 114 that will be processed by an electronic delay generator 116 (FIG. 3) and utilized to control the TDLAS or other type of spectroscopy system as described below.

Figure 4:
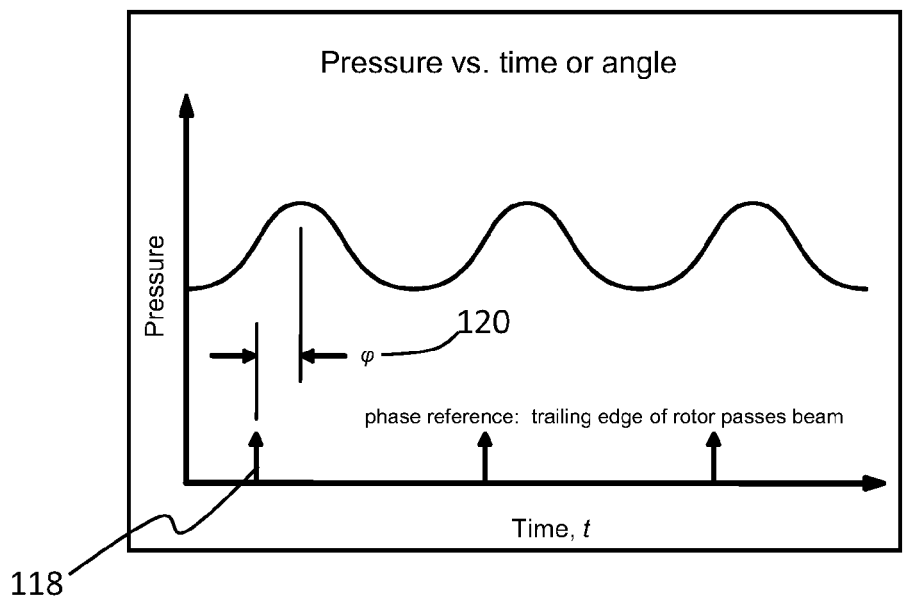
FIG. 4 is a block diagram of a spectroscopy system.

For example, as shown in FIG. 4, the pressure at a fixed location in between spinning compressor rotor blades and a fixed stator varies as each rotor blade passes the stator. As illustrated in FIG. 2, the synchronization time beam 112 is periodically blocked and extinguished by each rotor blade passing in front of the detector 110 on a stator 104. An electronic edge transition (graphically illustrated as element 118) is captured in the synchronization time signal 114 generated by the detector 110 and delay generator 116 when the synchronization pulse is blocked. The electronic edge transition 118 can thus be used as the start trigger for a highly accurate time signal with variable phase time delay $\phi$ 120. This time-delayed synchronization signal 114 can, in turn, be used to control an absorption spectroscopy system 122.

Figure 2:
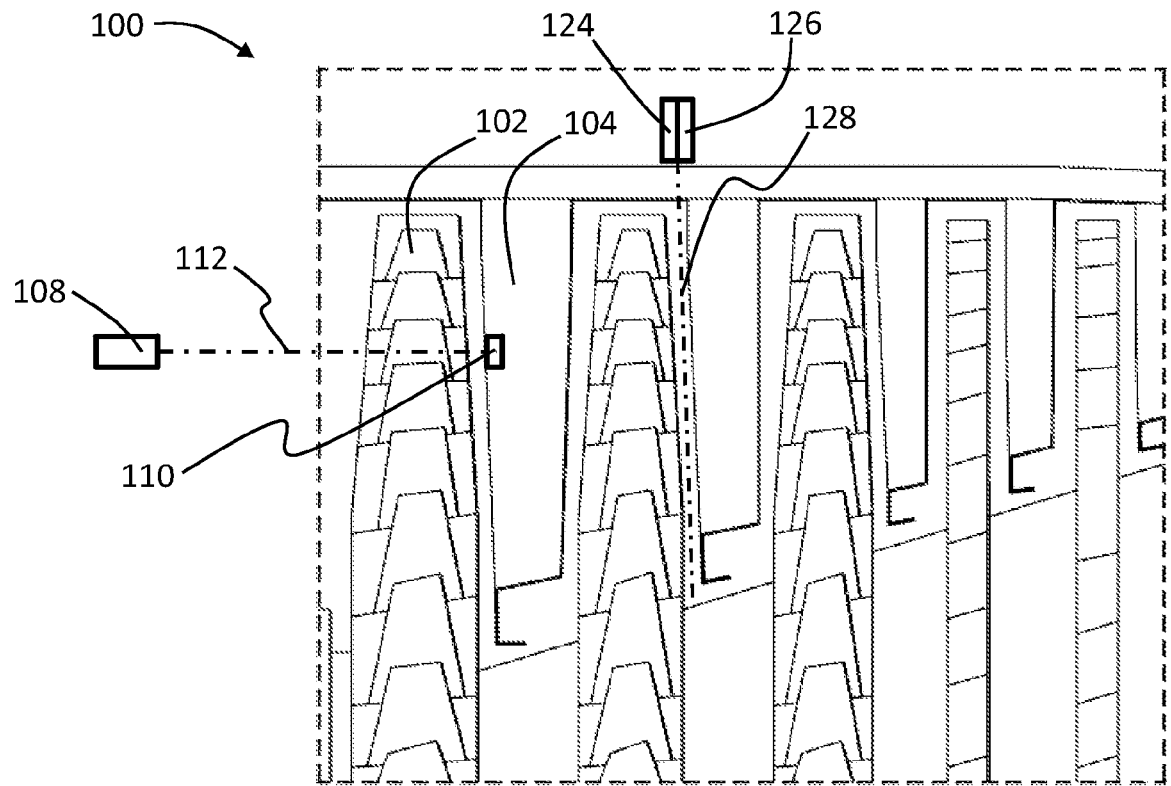
FIG. 2 is a detailed schematic diagram of the compressor and stator zone of the gas turbine engine of FIG. 1.

In particular, as illustrated in FIG. 2, one or more TDLAS systems 122 having a laser 124 and detector 126 may be optically associated with a location of interest. For example, as illustrated on FIG. 2, the location of interest may be the compressor section of the gas turbine engine. A laser spectroscopy probe beam 128 will travel through the zone of interest to a spinning hub or other surface radially in between the compressor and fixed stator blades. A single line of sight spectroscopy probe beam 128 is shown but in many cases multiple lines of sight will be required in order to allow tomographic reconstruction of the two dimensional, time dependent pressure or temperature distribution of interest. It is important to note that the configuration shown on FIG. 2 is a representative configuration only. For example, the placement of the laser 124 and detector 126 elements illustrated on FIG. 2, such that the probe beam 128 is reflected off of the engine hub and received at the detector is only one possible configuration for probing the compressor section of a jet engine. The laser and detector elements (or multiple laser and detector elements) can be arranged in any manner suited to adequately probe the system of interest.

As noted above, the time-delayed synchronization signal 114 generated by the synchronization system 100 can be used to initiate a series of two or more DFB laser scans. Phase-locking the series of laser spectroscopy wavelength scans to a particular repetitive time event shifts the burden of providing accurate temporal resolution from the duration of the laser scan itself to the time delay electronics that initiate the laser scan.

Using phase locking as described above allows the laser to be scanned slowly across relevant wavelengths, if desired. In a relatively slow scanning case, an appropriate phase delay is chosen and a wavelength scan occurs. Depending on how quickly the laser wavelength scan is completed, several rotor blades (and several corresponding pressure transients), may pass by the spectroscopy probe beam 128 during a single wavelength scan. However, the phase locking system assures that the next scan will not begin until the identical phase relationship between the probe beam 128 and the next rotor blade passing occurs. Therefore, the data for one or more subsequent scans will be synchronized with every other scan at a given point in the phase delay.

Provided that the turbine does not change rotation speed during the series of spectroscopy scans, this technique can provide the required temporal resolution to achieve measurements impossible when relying on the DFB scan rate alone for temporal resolution. When sufficient averaging has occurred at a first phase delay, a new phase delay is chosen and the process is repeated until the entire range of phases is filled in. Thus a detailed pressure or temperature model may be determined with known spectroscopy methods by the spectroscopy processor 130 over a time frame that is relatively longer than the fluctuations in the parameter being measured. Accordingly, the temporal resolution of the spectroscopy system 122 is not set by how quickly the laser is scanned but by the resolution of the electronic phase delay generator 116 and how much jitter there is at a particular phase delay setting. In general the phase delay resolution will be several orders of magnitude finer than can be achieved by scanning the laser as rapidly as possible and the jitter will be very small; this technique will therefore give much better temporal resolution than reliance on the laser scan rate.

A limiting case of slow wavelength scan phase-locked TDLAS measurements occurs when the laser is tuned in a "step and measure" fashion. In this case, the laser is tuned to a specific wavelength and measurements are made at a range of phase delays. When sufficient averaging at a particular phase delay is complete, a new phase delay is selected and the laser is tuned to the next wavelength. In this way, spectra are obtained by scanning the phase delay quickly rather than the wavelength. This is one particularly useful method of obtaining the necessary temporal measurements.

In addition, in order to "map" the pressure or temperature field, after measurements are made at a particular location, the probe beam 128 may be moved to a new location where additional measurements are made until the entire area of interest is mapped. Alternatively a spectroscopic system could be implemented with multiple probe beams and detectors, all coordinated by a single synchronization system.

Figure 5:
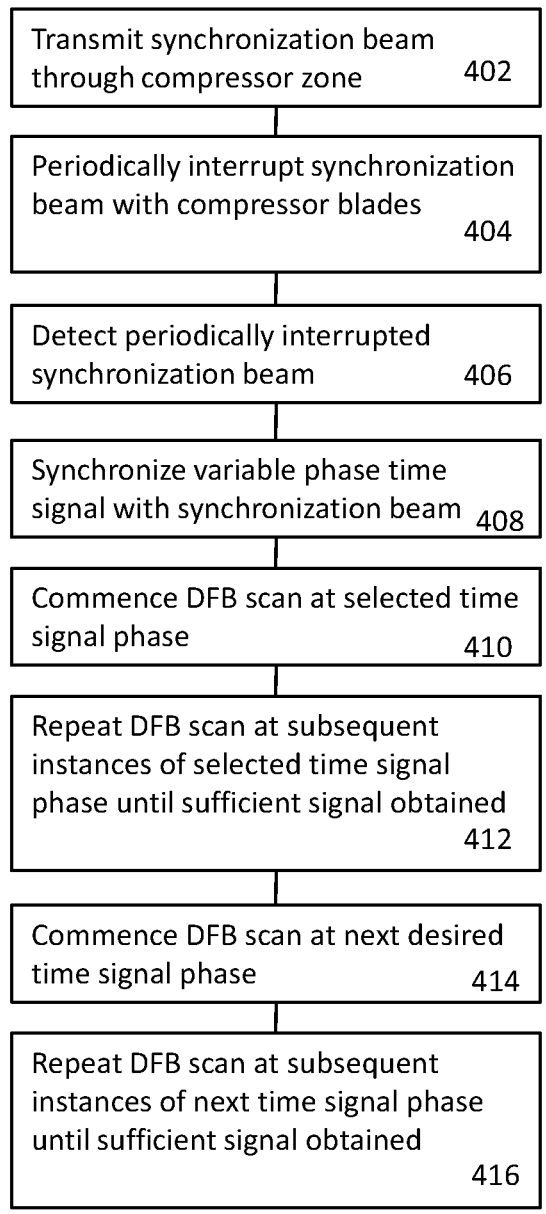
FIG. 5 is a flow chart illustrating one method disclosed herein.

An alternative embodiment disclosed herein is a method of spectroscopically measuring a transient parameter in a system with rapidly moving parts and highly variable gas parameters, such as a gas turbine engine. As shown on FIG. 5, the method includes an initial step of transmitting a synchronization beam through a compressor zone. (step 402) Next the synchronization beam maybe periodically interrupted, extinguished, reflected, refracted or otherwise disturbed with a rapidly moving mechanical part such as the compressor rotor blades of a jet engine. (step 404) The synchronization beam may then be detected with a suitable detector. (step 406)

The electric output of the detector may then be utilized by an electronic delay generator to create a variable phase time signal. (step 408) The variable phase time signal may be used to control the commencement of a DFB spectroscopy laser wavelength scan at a selected time signal phase. (step 410)

The DFB spectroscopy laser wavelength scan may be repeated at subsequent instances of the same time signal phase until sufficient signal is obtained to perform a spectroscopic analysis. (step 412) A series of DFB scans may also be performed at subsequent different time signal phases to fully probe the transient gas parameter at the location of interest. (step 414) Individual scans performed at each time signal phase may be repeated as required until sufficient data is obtained for spectroscopic analysis. (step 416)

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

What is claimed is:

1. A method of TDLAS measurement comprising:
providing a synchronization light source and synchronization detector; transmitting light from the synchronization light source to the synchronization detector;

periodically interrupting the light transmitted from the synchronization light source to the synchronization detector;

generating a repeating time signal from the electrical output of the synchronization detector;

initiating a first DFB spectroscopy laser wavelength scan at a selected phase delay according to the time signal; wherein a duration of the first DFB spectroscopy laser wavelength scan exceeds the duration of the repeating time signal; and initiating at least a second DFB laser spectroscopy wavelength scan at a subsequent instance of the selected time signal phase delay; wherein a duration of the second DFB spectroscopy laser wavelength scan exceeds the duration of the repeating time signal.

2. The method of TDLAS measurement of claim 1 further comprising averaging the results of at least the first and second DFB spectroscopy laser wavelength scans.

3. The method of TDLAS measurement of claim 2 further comprising determining a parameter of interest from the averaged results of the first and second DFB spectroscopy laser wavelength scans.

4. The method of TDLAS measurement of claim 3 wherein the parameter of interest is a local gas pressure or a local gas temperature.

5. The method of TDLAS measurement of claim 2 further comprising:
initiating a third DFB spectroscopy laser wavelength scan at a second and different time signal phase delay; and
initiating a fourth DFB spectroscopy laser wavelength scan at a subsequent instance of the second time signal phase delay.

6. The method of TDLAS measurement of claim 5 further comprising averaging the results of at least the first, second, third and fourth DFB spectroscopy laser wavelength scans.

7. The method of TDLAS measurement of claim 6 further comprising determining a parameter of interest from the averaged results of the first and second DFB spectroscopy laser wavelength scans.

8. The method of TDLAS measurement of claim 7 wherein the parameter of interest is a local gas pressure or a local gas temperature.

9. The method of TDLAS measurement of claim 7 wherein the parameter of interest is a local gas pressure or a local gas temperature and the determination shows a variation of the parameter of interest over time.

10. A TDLAS apparatus comprising:
a spectroscopic probe laser source and spectroscopic detector; and
a synchronization light source and synchronization detector.

11. The TDLAS apparatus of claim 10 further comprising an electronic delay generator wherein the electronic delay generator receives input from the synchronization detector and provides a synchronization signal to control the spectroscopic probe laser source.

12. The TDLAS apparatus of claim 11 further comprising a data processor configured to determine a parameter of interest from the output of the spectroscopic detector according to an absorption spectroscopy method.

13. A method of measuring a local transient pressure in a gas turbine engine comprising:
providing a synchronization light source and synchronization detector;
transmitting light from the synchronization light source to the synchronization detector;
periodically interrupting the light transmitted from the synchronization light source to the synchronization detector with a moving part of the gas turbine engine;
generating a repeating time signal from the electrical output of the synchronization detector;
initiating a first DFB spectroscopy laser wavelength scan at a selected phase delay according to the repeating time signal; and
initiating at least a second DFB laser spectroscopy wavelength scan at a subsequent instance of the selected time signal phase delay;
averaging the results of at least the first and second DFB spectroscopy laser wavelength scans;
determining a local pressure from the averaged results of the first and second DFB spectroscopy laser wavelength scans with a absorption spectroscopy method.

14. The method of measuring a local transient pressure of claim 13 further comprising:
initiating a third DFB spectroscopy laser wavelength scan at a second and different time signal phase delay; and
initiating a fourth DFB spectroscopy laser wavelength scan at a subsequent instance of the second time signal phase delay.

15. The method of measuring a local transient pressure of claim 14 further comprising:
averaging the results of the third and second DFB spectroscopy laser wavelength scans;
determining a variation in the local pressure from the averaged results of the first second, third and fourth DFB spectroscopy laser wavelength scans with a absorption spectroscopy method.

* * * * *